United States Patent [19]

Stricker et al.

[11] Patent Number: 5,302,693

[45] Date of Patent: Apr. 12, 1994

[54] PROCESS FOR PREPARING POLY-D,L-LACTIDE AND THE USE THEREOF AS A CARRIER FOR ACTIVE SUBSTANCES

[75] Inventors: Herbert Stricker, Neckargemund; Dieter Bendix, Ingelheim am Rhein, both of Fed. Rep. of Germany

[73] Assignee: Boehringer Ingelheim GmbH, Ingelheim am Rhein, Fed. Rep. of Germany

[21] Appl. No.: 717,562

[22] Filed: Jun. 19, 1991

[30] Foreign Application Priority Data

Jun. 23, 1990 [EP] European Pat. Off. ......... 90111954.5
Sep. 11, 1990 [DE] Fed. Rep. of Germany ....... 4028764

[51] Int. Cl.$^5$ ............................................. C08G 63/08
[52] U.S. Cl. .................................. 528/354; 525/415; 525/450; 528/361
[58] Field of Search ................ 528/354, 361; 525/415, 525/450; 623/11; 424/489

[56] References Cited

U.S. PATENT DOCUMENTS

| 4,719,246 | 1/1988 | Murdoch et al. | 525/415 |
| 4,766,182 | 8/1988 | Murdoch et al. | 525/415 |
| 4,789,726 | 12/1988 | Hutchinson | 528/354 |
| 4,800,219 | 1/1989 | Murdoch et al. | 525/415 |
| 4,902,515 | 2/1990 | Loomis et al. | 424/486 |
| 5,061,281 | 10/1991 | Mares et al. | 528/354 |

*Primary Examiner*—John Kight, III
*Assistant Examiner*—Shelley A. Dodson
*Attorney, Agent, or Firm*—David E. Frankhouser; Alan R. Stempel; Mary-Ellen M. Timbers

[57] ABSTRACT

The invention relates to a process for preparing poly-D,L-lactide and its use as a carrier for active substances.

2 Claims, No Drawings

PROCESS FOR PREPARING POLY-D,L-LACTIDE AND THE USE THEREOF AS A CARRIER FOR ACTIVE SUBSTANCES

FIELD OF THE INVENTION

The invention relates to a new process for preparing low molecular weight poly-D,L-lactides and the use thereof as active substance carriers for pharmaceutical compositions.

BACKGROUND OF THE INVENTION

From the prior art, numerous active substance release systems based on resorbable polymers are known which are injected or implanted. These systems are always preferred when the active substance has to be released over a fairly long period and oral administration is impossible or is not sufficiently reliable or effective. A resorbable implant which contains active substance is also preferred to oral administration when the active substance has to be released within a specific area of the body, as in the case, for example, with powerful cytostatics used on tumours.

Implantable active substance carriers should satisfy the following criteria:

The active substance should be released at a constant rate over a fairly long period of time and the polymer carrier should be broken down within a reasonable time so that there is no need for the implant to be surgically removed after the active substance has been released. Important parameters in connection with this are the swellability (water uptake), the reduction in molecular mass and the reduction in the mass of the polymer.

Processes for preparing poly-D,L-lactide, e.g. by polymerisation of lactide in the presence of suitable polymerisation catalysts (higher molecular masses) or by the polycondensation of lactic acid (lower molecular masses) are part of the prior art.

The term "poly-lactic acid" in this case refers to polymers synthesised from lactic acid units and having a low level of polymerisation. Poly-lactic acids of this kind are usually prepared by condensation of lactic acids but are also obtained in the ring-opening polymerisation of lactides under suitable conditions.

DESCRIPTION OF THE INVENTION

It has been found surprisingly, that an implantable active substance carrier prepared from a poly-D,L-lactide of average molecular mass according to the following method has particular advantages.

The process according to the invention is characterised in that D,L-lactide is polymerised in the presence of suitable polymerisation catalysts with the addition of defined amounts of poly-lactic acid.

Suitable polymerisation catalysts are known from the prior art, e.g. organic and inorganic tin compounds such as tin lactate, tin tartrate, tin oxylate, tin dicaprylate, tin dilaurate, tin dipalmitate, tin chloride etc. Tin dioctoate, more accurately referred to as tin di-(2-ethyl-hexanoate), is particularly preferred.

The amount of poly-lactic acid (preferably poly-D,L-lactic acid) added is between 5 and 40, preferably between 20 and 30%, based on the D,L-lactide used. According to the invention, the term poly-lactic acid refers to poly-D-, Poly-L- or Poly-D,L-lactic acid. The poly-lactic acid used should have an average molecular weight, determined by titration of terminal groups, of about 1,800 to 2,500 (numerical units).

The units by weight, determined by gel permeation chromatography against narrowly distributed polystyrene standards, should be between 3000 and 4000 and the polydispersity should range from about 2.5 to 3.5.

Poly-D,L-lactide prepared by the process according to the invention, with an inherent viscosity (i.V.) measured in chloroform at 25° C., c=100 mg/100 ml, of between 0.15 and 0.25, preferably 0.17 to 0.20 dl/g, molecular mass by weight (Mw)—based on narrowly distributed polystyrene standards in chloroform—of between $1 \times 10^4$ and $1.4 \times 10^4$, preferably $1.2 \times 10^4$, polydispersity D: 1.7 to 2.0, is suitable for preparing the implantable active substance carriers according to the invention.

Polymers produced by the process according to the invention and implants made from them have the following advantages.

1) Fusion characteristics: low melting range, preferably 60°–75° C. Consequently the temperature of the mass remains low during processing by extrusion.

2) Glass transition temperature (Tg): The polymers produced according to the invention maintain a Tg of about 45° C., i.e. above body temperature, for about 30 days. Implants made of these polymers therefore keep their original mechanical state for this length of time and thus ensure constant conditions of release.

3) Swelling characteristics: By contrast with poly-(D,L-lactide-co-glycolide), the poly-D,L-lactide produced according to the invention only begins to absorb water in larger quantities after 35 days. In the case of poly- (D,L-lactide-co-glycolide) (molar ratio 1:1, i.V. about 0.4) this occurs after only about 8 days. This property is of major importance to the stability of incorporated active substances which are prone to hydrolysis.

4) Reduction in molar mass: The polymers produced according to the invention exhibit a significant reduction in molar mass only after about 10 days and are therefore more suitable for preparing release systems with constant release characteristics. It is of great importance, for the release of active substance, that in e.g. an implant, the breakdown of the polymer should occur more rapidly on the inside than on the outer surface exposed to the aqeuous medium. As a result, a barrier is formed, the permeability of which controls the release of the incorporated active substances and polymer breakdown products.

5) Reduction in mass: About 35 days after being placed in phosphate buffer (isotonic, pH 7.4; 37° C.) there is no reduction in mass, subsequently within about 40 days the polymer is broken down completely into lactic acid.

The implants consisting of the polymers prepared according to the invention may be produced by various methods, e.g. by extrusion (I) or by the solution method (II).

For I: Poly-D,L-lactides with inherent viscosities of between 0.15 and 0.25 have a low melting range and can therefore be processed by extrusion with numerous pharmaceutical substances without causing thermal decompositions thereof. For this purpose the polymer in powder or granule form is mixed with the active substance and made into briquettes. If desired, other exipients such as water soluble pore forming agents such as lactose may be added. The mixture is then extruded and cut into pieces (e.g. cylinders 2 mm in diameter and 2 cm long).

For II: In the solution method, the polymer and any excipients such as plasticisers are dissolved in a suitable solvent, poured out as films or into moulds, then dried and further processed. In this regard the following embodiments are possible:

A) solid bars,
B) rolled films,
C) coated bars,
D) tubular members
E) coated tubular members All the embodiments of the implant according to the invention may be made up of several layers. For example, Form A may be produced by the following method:

The active substance is dissolved or suspended in the polymer solution (e.g. with ethyl acetate, acetone or some other pharmacologically acceptable solvent). If necessary, pharmaceutical excipients such as water soluble pore forming agents or plasticisers may be added as well as the active substance. The solution or suspension is then poured out on to a defined surface and dried in vacuo until a residual solvent content of possibly 3 to 6% is obtained. Apparatus and processes for producing such films are known to those skilled in the art and require no further explanation. Multi-layered castings are obtained by the repeated application of polymer solution (with or without active substance). The preferred layer thickness is in the range from 200 to 300 μm.

Finally, bars of the desired widths and lengths are cut under aseptic conditions.

Rolls of Type B consist of single- or multi-layer polymer films in which the active substance may be contained in only one layer or in every layer and the thickness of the films is generally between 30 and 500 μm, preferably 70 to 90 μm. After drying, the films are cut up and shaped into rolls of suitable dimensions, e.g. 3 cm long. By joining a plurality of film layers it is readily possible to combine active substances and produce defined concentration profiles, so that the individual layers have different rates of release.

EXAMPLE 1

40, 35 and 30 g of D,L-lactide as well as 10 (20%), 15 (30%) and 20 g (40%) of poly-D,L-lactic acid are weighed into heated 2-necked flasks in a glove box under dry nitrogen. The poly-lactic acid added (PLA) had the following analytical data:

$M_n$=2000 (Terminal group titration).
$M_n$=1100 (GPC, ND-PS standards).
$M_w$=3400 (GPC, ND-PS standards).
Content of D,L-lactide: 2% (NMR, $CDCl_3$, 250 MHz).
Water content: 0.2% (KF-titration).

The mixture was melted at 130° C. under dry nitrogen and then 25.6 mg of tin octoate in toluene solution were added as catalyst. A sample was taken every hour and the inherent viscosity (i.V) was determined. (c=0.1 g/10 ml, chloroform, 25° C.).

| Reaction time [h] | 20% PLA i.V [dl/g] | 30% PLA i.V [dl/g] | 40% PLA i.V [dl/g] |
| --- | --- | --- | --- |
| 1 | .08 | .07 | .08 |
| 2 | .12 | .09 | .07 |
| 3 | .16 | .11 | .09 |
| 4 | .18 | .13 | .09 |
| 5 | .20 | .14 | .10 |
| 6 | .21 | .15 | .11 |
| 7 | .22 | .15 | .11 |

EXAMPLE 2

400 g of D,L-lactide and 100 g of poly-D,L-lactic acid were weighed into a flask in a glove box under dry nitrogen. The mixture was melted under 140° C. with stirring and under a covering a dry nitrogen, the oil bath temperature was lowered to 130° C. and 256 mg of tin octoate in toluene solution were added as catalyst. The glassy polymer melt obtained after 5 hours' polymerisation was analysed:

Inherent viscosity: 0.17 dl/g.
Residual Monomer content: 10.5% (NMR, $CDCl_2$, 250 MHz).
$M_w$ 13 500 (GPC, PS-standards, $CHCl_3$).
$M_n$ 6 200 (GPC, PS-standards, $CHCl_3$).
Polydispersity Mw/Mn 2.2.

The polymer was then dissolved in four times the amount of acetone, with rigorous stirring at boiling point, re-precipitated from water and dried in a vacuum drying cupboard at 30° C.

Inherent viscosity: 0.18 dl/g

EXAMPLE 3

7.5 kg of D,L-lactide and 2.5 kg of poly-D,L-lactic acid were placed in a helical mixer and melted under nitrogen. 5 g of tin octaoate in 20 ml of toluene were added and the mixture was polymerised for 5 hours at an oil bath temperature of 170° C.

Yield: 98% of material put in.

The polymer was dissolved in 50 l of acetone at boiling point, filtered, precipitated from water and dried at 38° C. in a vacuum drying cupboard.

Yield: 77% of material put in.
Inherent viscosity: 0.19 dl/g.
Residual monomer content: <<1% (NMR, $CDCl_3$, 250 MHz).

What is claimed is:

1. An improved process for preparing poly-D,L-lactide wherein D,L-lactide is polymerized by ring-opening polymerization in the presence of a polymerization catalyst, wherein the improvement comprises performing such reaction with the concurrent addition of about 5 to 40% by weight of poly-lactic acid, based upon the amount of D,L-lactide.

2. The process according to claim 1, wherein between about 20 to 30% by weight of poly-lactic acid, based on the amount of D,L-lactide, is added to the reaction.

* * * * *